United States Patent [19]
Jackson et al.

[11] Patent Number: 5,383,874
[45] Date of Patent: Jan. 24, 1995

[54] SYSTEMS FOR IDENTIFYING CATHETERS AND MONITORING THEIR USE

[75] Inventors: Jerome Jackson, Sunnyvale; Roger A. Stern, Cupertino, both of Calif.

[73] Assignee: EP Technologies, Inc., Sunnyvale, Calif.

[21] Appl. No.: 976,691

[22] Filed: Nov. 13, 1992

Related U.S. Application Data

[63] Continuation-in-part of Ser. No. 790,578, Nov. 8, 1991, abandoned.

[51] Int. Cl.6 .............................................. A61B 17/36
[52] U.S. Cl. .......................................... 606/1; 606/34; 606/41; 606/42; 606/38
[58] Field of Search ................... 606/1, 32–35, 606/41, 42, 10–12, 45–50, 38; 604/20, 21

[56] References Cited

U.S. PATENT DOCUMENTS

| | | | |
|---|---|---|---|
| 3,929,137 | 12/1975 | Gonser | 606/45 |
| 4,051,855 | 10/1977 | Schneiderman | 606/42 |
| 4,580,557 | 4/1986 | Hertzmann | 606/12 |
| 4,936,842 | 6/1990 | D'Amelio et al. | 606/42 |

Primary Examiner—Stephen C. Pellegrino
Assistant Examiner—M. Peffley
Attorney, Agent, or Firm—Ryan, Kees & Hohenfeldt

[57] ABSTRACT

A catheter carries a functional component, like an ablating electrode, having a predetermined operating characteristic. The catheter also electronically retains an identification code that uniquely identifies the predetermined operating characteristic. The catheter is capable of transmitting the identification code to an external reader in response to a predetermined prompt. An associated apparatus, like an ablating energy source, reads the identification code and compares it to predetermined operating criteria. The apparatus will not permit interaction with the functional catheter component, if the identification code indicates that the functional characteristics of the catheter are not suited for the intended interaction. The catheter can also store usage information, to prevent reuse.

21 Claims, 5 Drawing Sheets

SYSTEMS FOR IDENTIFYING CATHETERS AND MONITORING THEIR USE

This application is a continuation in part of copending application Ser. No. 07/790,578, filed Nov. 8, 1991, now abandoned.

FIELD OF THE INVENTION

The invention generally relates to catheters and associated power sources. In a more specific sense, the invention relates to ablation catheters and ablation methods that transmit energy to form lesions for therapeutic purposes.

BACKGROUND OF THE INVENTION

Physicians make use of catheters today in medical procedures to gain access into interior regions of the body to ablate targeted tissue areas. It is important for the physician to control carefully and precisely the emission of energy within the body used to ablate the tissue.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery (which is typically the femoral vein or artery) into the interior region of the heart that is to be treated. The physician then further manipulates a steering mechanism to place the electrode carried on the distal tip of the catheter into direct contact with the tissue that is to be ablated. The physician directs radio frequency energy from the electrode tip through tissue to an indifferent electrode to ablate the tissue and form a lesion.

Cardiac ablation especially requires the ability to precisely monitor and control the emission of energy from the ablation electrode.

SUMMARY OF THE INVENTION

The invention provides systems and apparatus for identifying catheters and monitoring their use.

One aspect of the invention provides a catheter including a body carrying a functional component, like an ablating electrode, having a predetermined operating characteristic. The body also carries electronic means for retaining an identification code that uniquely identifies the predetermined operating characteristic of the functional component. The electronic retaining means includes an output for transmitting the identification code to an external reader in response to a predetermined prompt.

Another aspect of the invention provides a catheter with a functional component, like an ablating electrode. In this aspect of the invention, the body also carries electronic means for retaining a code that represents the usage of the functional component. The electronic retaining means includes an output for generating the usage code in response to a predetermined prompt and an input for updating the usage code in response to use of the functional component.

Another aspect of the invention provides an apparatus for interacting with the functional component of the catheter. The apparatus includes a mechanism that prompts the electronic retaining means of the catheter to generate its identification code. The apparatus also stores predetermined criteria governing its interaction with the catheter. The apparatus compares the generated identification code to the predetermined interaction criteria. The apparatus generates a first control signal when the generated identification code meets the predetermined interaction criteria. The apparatus generates a second control signal, different than the first control signal, when the generated identification code does not meet the predetermined interaction criteria.

In one embodiment, the apparatus will not permit the intended interaction with the functional catheter component, if the identification code indicates that the catheter has been used too many times or if the functional characteristics of the catheter are not suited for the intended interaction.

In a preferred embodiment, the functional catheter component is an ablating electrode, and the apparatus is a source of ablating energy. In this embodiment, the apparatus sets the operating ablating power conditions depending upon the particular functional characteristics of the associated ablating electrode. In this way, the apparatus distinguishes among ablating electrodes of different functional characteristics and supplies ablating power accordingly.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
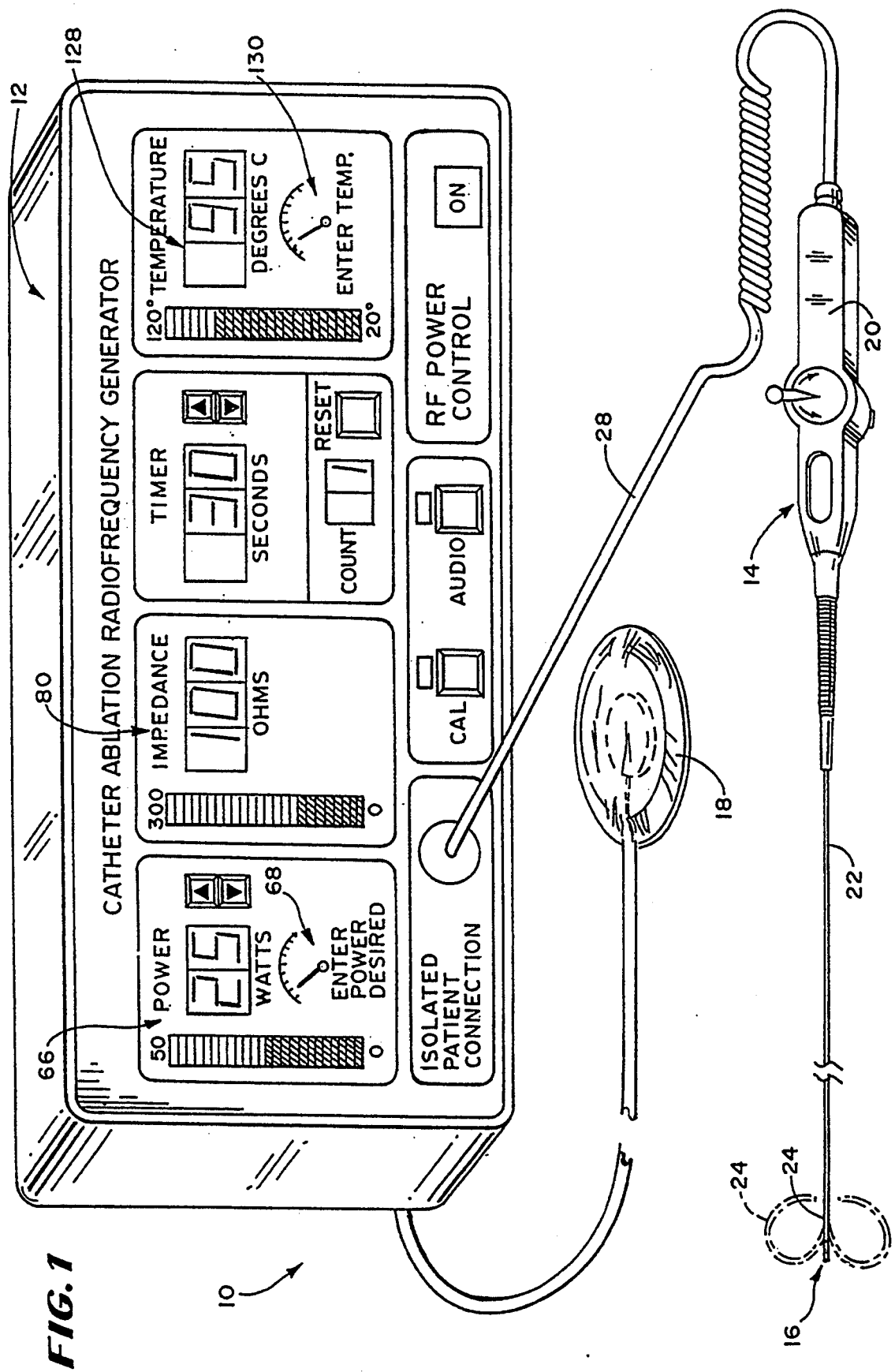
FIG. 1 is a perspective view of a system for ablating tissue that embodies the features of the invention.

FIG. 1 shows a system 10 for performing ablation on human tissue that embodies the features of the invention. The system 10 includes a radiofrequency generator 12 that delivers radiofrequency energy. The system 10 also includes a steerable catheter 14 carrying a radiofrequency emitting tip electrode 16.

In the illustrated embodiment, the system 10 operates in a monopolar mode. In this arrangement, the system 10 includes a skin patch electrode that serves as an indifferent second electrode 18. In use, the indifferent electrode 18 attaches to the patient's back or other exterior skin area.

Alternatively, the system 10 can be operated in a bipolar mode. In this mode, the catheter 14 carries both electrodes.

In the illustrated embodiment, the ablation electrode 16 and indifferent electrodes 18 are made of platinum.

The system 10 can be used in many different environments. This specification describes the system 10 when used to provide cardiac ablation therapy.

When used for this purpose, a physician steers the catheter 14 through a main vein or artery (typically the femoral vein or artery) into the interior region of the heart that is to be treated. The physician then further manipulates the catheter 14 to place the tip electrode 16 into contact with the tissue within the heart that is targeted for ablation. The user directs radio frequency energy from the generator 12 into the tip electrode 16 to form a lesion on the contacted tissue.

In the embodiment shown in FIG. 1, the catheter 14 includes a handle 20, a guide tube 22, and a tip 24, which carries the tip electrode 16 (which also will be called the ablation electrode). The handle 20 encloses a steering mechanism 26 for the catheter tip 24. A cable 28 extending from the rear of the handle 20 has plugs (not shown). The plugs connect the catheter 14 to the generator 12 for conveying radiofrequency energy to the ablation electrode 16. The radiofrequency energy heats the tissue to form the lesion.

Left and right steering wires (not shown) extend through the guide tube 22 to interconnect the steering mechanism 26 to the left and right sides of the tip 24. Rotating the steering mechanism 26 to the left pulls on the left steering wire, causing the tip 24 to bend to the left. Also, rotating the steering mechanism 26 to the right pulls on the right steering wire, causing the tip 24 to bend to the right. In this way, the physician steers the ablation electrode 16 into contact with the tissue to be ablated.

The generator 12 includes a radiofrequency power source 30 connected through a main isolation transformer 32 to first and second conducting lines 34 and 36.

In the illustrated environment, the power source 30 delivers up to 50 watts of power at a frequency of 500 kHz. The first conducting line 34 leads to the ablation electrode 16. The second conducting line 36 leads to the indifferent patch electrode 18.

Figure 2:
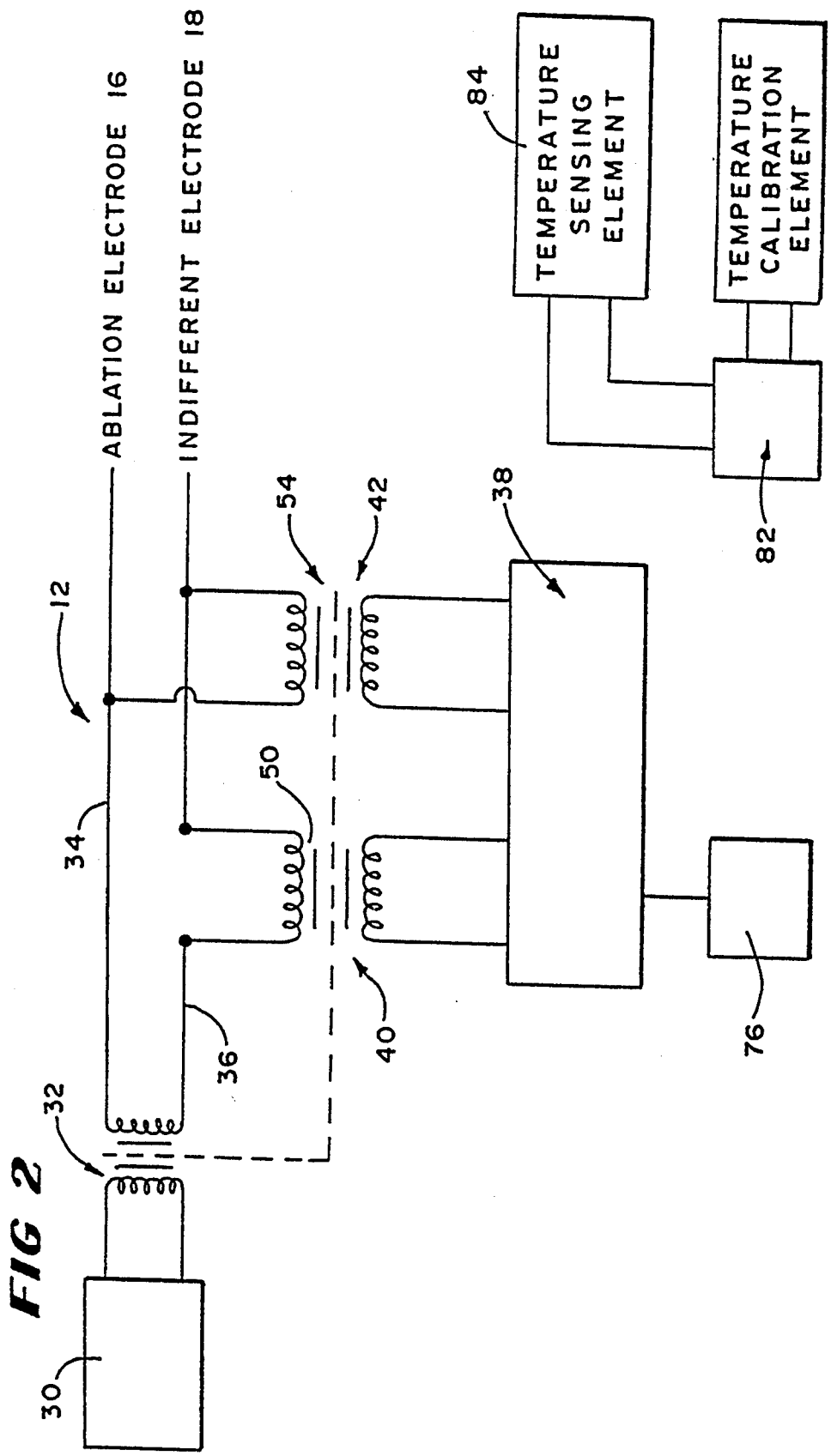
FIG. 2 is a schematic view of the generator and associated monitor and control circuits for the system.
Figure 3:
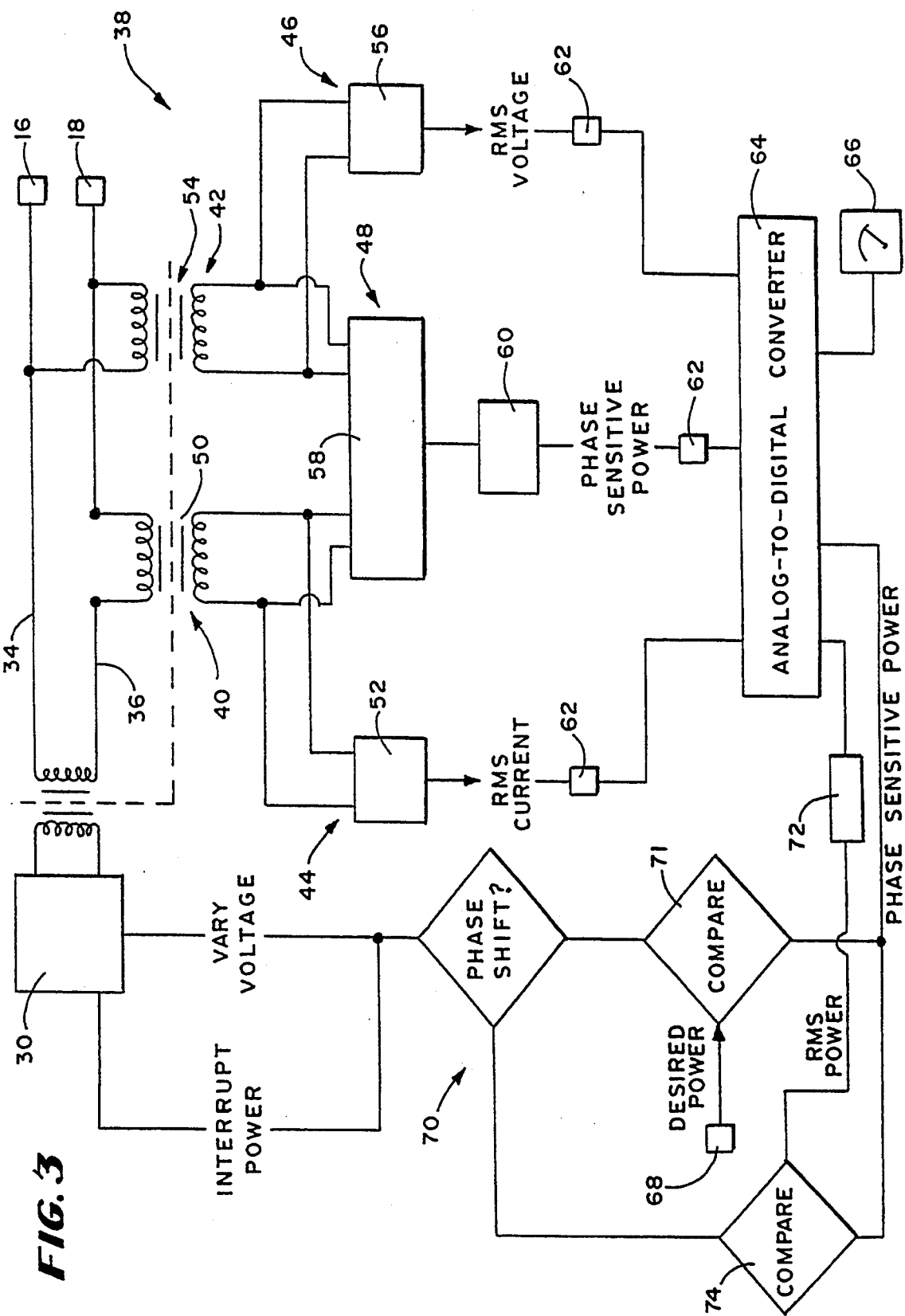
FIG. 3 is a schematic view of the power monitor and control circuit for the system.

As FIGS. 2 and 3 show, the system 10 includes first monitoring means 38 for measuring the radiofrequency current and radiofrequency voltage delivered by the generator 12 to the patient. The first monitoring means 38 also derives control signals indicative of RMS (root mean squared) voltage (in volts), RMS current (in amps), and actual phase sensitive power (in watts) to support other control functions of the generator 12.

The first monitoring means 38 may be variously configured and constructed. In the illustrated embodiment, the first monitoring means 38 includes current monitoring means 40 for measuring the radiofrequency current passing from the first line 34 through the tissue to the second line 36 (i.e., from the ablation electrode 16 to the indifferent patch electrode 18).

The first monitoring means 38 also includes voltage monitoring means 42. The voltage monitoring means 42 measures the radiofrequency voltage generated between the first and second conducting lines 34 and 36 (i.e., between the ablation electrode 16 and the indifferent patch electrode The first monitoring means 38 includes three control outputs 44, 46, and 48.

The first control output 44 carries a signal representative of RMS current conducted by the ablation electrode 16.

The second control output 46 carries a signal representative of the RMS voltage between the ablation electrode 16 and the indifferent patch electrode 18.

The third control output 48 carries a signal representative of actual phase sensitive power transmitted by the ablation electrode 16.

In the illustrated embodiment (as FIGS. 2 and 3 show), the current monitoring means 40 includes an isolated current sensing transformer 50 connected in the second conducting line 36. In this arrangement, the current sensing transformer 50 directly measures the radiofrequency current passing through the ablation electrode 16 to the indifferent patch electrode 18.

The measured value is a radiofrequency signal varying at the selected rate, which in the illustrated embodiment is 500 kHz.

The current sensing transformer 50 is connected to the first control output 44, which derives RMS current. The first control output 44 includes an integrated circuit RMS converter 52 to do this function. The RMS current converter first squares the radiofrequency current input signal from the current sensing transformer 50, and then averages the squared signal over a user prescribed period (which in the illustrated embodiment is about once every 0.01 second). The RMS current converter 52 then takes the square root of the average squared value. The resulting output represents RMS current.

The RMS current signal takes the form of a relatively slowly varying signal, compared with the rapidly varying radiofrequency current input signal.

As FIGS. 2 and 3 show, the voltage monitoring means 42 includes an isolated voltage sensing transformer 54 that is connected between the first and second conducting lines. In this arrangement, the voltage sensing transformer 54 directly measures the radiofrequency voltage across the body tissue between the ablation electrode 16 and the indifferent patch electrode 18.

Like the value measured by the current sensing transformer 50, the measured voltage value is a radiofrequency signal varying at the selected 500 kHz rate.

The voltage sensing transformer 54 is connected to the second control output 46, which derives RMS voltage. The second control output 46 includes an integrated circuit RMS converter 56 to do this function. The RMS voltage converter 56 squares the radiofrequency voltage input signal and then averages it over the same user prescribed period used by the current converter 52. The RMS voltage converter 56 then takes the square root of the average squared voltage value.

The resulting RMS voltage signal (like the RMS current signal) takes the form of a relatively slowly varying signal.

The voltage sensing transformer 54 is also connected to the third control output 48, which derives actual phase sensitive power. The third control output 48 includes an analog multiplier integrated circuit 58 to do this function. The multiplier circuit 58 receives as one input the radiofrequency input current signal directly from the current sensing transformer 50. The multiplier circuit 58 also receives as a second input the radiofrequency input voltage signal directly from the voltage sensing transformer 54.

The output of the multiplier circuit 58 is the product of these two inputs, which represents the actual radiofrequency power transmitted by the ablation electrode 16.

The power value is (like its component current and voltage inputs) a radiofrequency signal varying at a relatively high radiofrequency rate.

The third control output 48 also includes a low pass filter 60. In the illustrated embodiment, which operates with a radiofrequency rate of 500 kHz, the cut off frequency of the filter 60 selected is about 100 Hz. The rapidly varying measured input power value is low pass filtered by the filter 60 into a relatively slowly varying signal.

This signal represents the actual phase sensitive power signal of the radiofrequency energy that the ablation electrode 16 delivers to the targeted tissue.

The first, second, and third control outputs 44, 46, and 48 each includes appropriate inline scaling circuits 62. The scaling circuits 62 scale the RMS current signal, the RMS voltage signal, and the actual phase sensitive power signal to a specified voltage range that can be usable by the remainder of generator 12 circuitry. In the illustrated embodiment, the scaled range is 0.0 to 5.0 volts.

The first monitoring means 38 also includes an analog to digital converter 64. The converter 64 digitizes a selected one or more of the analog RMS current output signal, RMS voltage output signal, and the actual phase sensitive power signal.

The digital output(s) of the converter 64 can be used to display measurement results. In the illustrated embodiment, the system 10 includes a first digital display 66 on the generator 12 to show the user the actual phase sensitive power signal.

The digital output(s) of the converter 64 also can be used to control operation of the generator 12. In the illustrated embodiment, the system 10 uses the digitized outputs in a feedback loop that maintains radiofrequency output voltage within a desired range or at a constant value to control radiofrequency power at the ablation electrode 16. By controlling the power delivered by the generator 12, the physician can reproducibly form lesions of the desired depth during an ablation procedure.

In this arrangement, the system 10 includes an input 68 for the user to enter an operating value desired for the actual phase sensitive power for the generator 12. The system 10 includes power control means 70 that includes comparator 71 to compare desired power with actual phase sensitive power. The output of the comparator varies the output voltage of radiofrequency power source 30 to maintain minimum error between the measured actual power and the set point power.

In the illustrated embodiment, the power control means 70 also monitors phase differences between radiofrequency voltage and current. The power control means 70 does this function by computing apparent power and by comparing the computed apparent power to the actual phase sensitive power. If the radiofrequency voltage and current signals are exactly in phase, the apparent power and actual phase sensitive power will be the same. However, if there is a phase difference, actual phase sensitive power will differ from the apparent power by a factor that represents the cosine of the phase angle.

In the illustrated embodiment, the power control means 70 includes a multiplier circuit 72 that obtains the product of the RMS current and RMS voltage. The resulting output of the multiplier circuit 72 forms the apparent (i.e., not phase sensitive) power of the system 10. The power control means 70 includes a comparator 74 to compare the derived apparent power with the actual phase sensitive power. The magnitude of the output of the comparator 74 quantifies the amount of the phase shift.

If the output of the phase shift comparator 74 exceeds a preselected amount, the power control means 70 generates a warning signal to show that a phase shift between the radiofrequency voltage and current has occurred. The system 10 may include a flashing light and audible alarm (not shown) to warn the user.

The power control means 70 operates to maintain a constant set power when the output of the phase shift comparator 74 remains within an allowable range above the threshold amount. The power control means 70 operates to reduce the output voltage of the source 30 when the output of the phase shift comparator 74 increases beyond this range. If the output of the phase shift comparator 74 shows a phase shift beyond a maximum threshold value, the power control means 70 generates a signal to shut off all power to the ablation electrode 16.

According to the invention, the system 10 also includes means 76 for identifying and monitoring the physical and/or functional characteristics of the catheter 14 that is connected to the radiofrequency generator 12.

The resulting control functions of the catheter identification means 76 can vary.

In one preferred arrangement (shown in FIG. 4), the identification means 76 assures that the catheter 14 and its intended use meet predetermined functional and therapeutic criteria.

In this embodiment, the identification means 76 senses the actual functional characteristics of the catheter 14 connected to the generator 12. The identification means compares these actual characteristics to the characteristics required for the intended use, based upon predetermined criteria. Based upon this comparison, the identification means 76 generates a variety of output control signals.

The control signals either actively control or passively monitor the operational characteristics of catheter 14 used in association with the power generator 12. The system 10 thereby guards against the use of a catheter 14 that does not meet the performance characteristics required.

More particularly, when the sensed physical and/or functional characteristics of the catheter 14 meet the predetermined use criteria, the output control signal generated by the identification means 76 actively permits the intended use of the catheter 14. Alternatively, the output control signal generates a passive, user discernible "Use Permitted" message under this condition. Still alternatively, the output control signal can simultaneously permit use while generating a confirming, user discernible message.

Likewise, when the sensed physical and/or functional characteristics of the catheter 14 do not meet the predetermined use criteria, the output control signal generated by the identification means 76 actively intervenes to prevent the intended use of the catheter 14. Alternatively, the output control signal generates a passive, user discernible "Use Not Permitted" alarm under this condition. Still alternatively, the output control signal can simultaneously prevent use while generating a confirming, user discernible alarm.

In another preferred arrangement (shown in FIG. 5), the identification means 76 generates signals that track the use of the catheter 12. This aspect of the invention guards against the reuse or overuse of a given catheter 14.

The particular details of these arrangements will now be discussed.

Controlling/Monitoring the Catheter-Generator Interface

Figure 4:
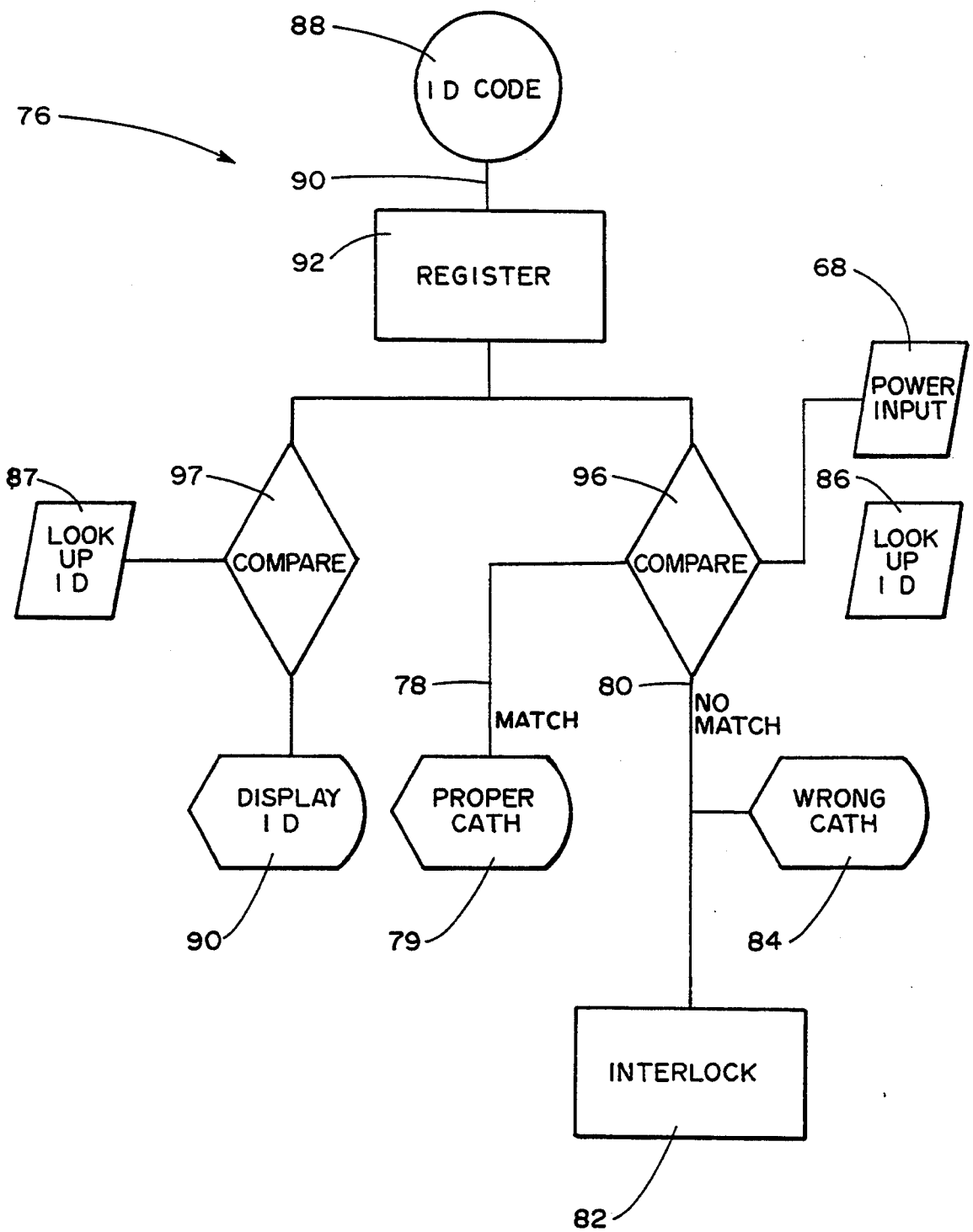
FIG. 4 is a schematic view of a catheter identification circuit that enables or prevents use of the catheter based upon functional and performance criteria.

In FIG. 4, the identification means 76 senses the actual physical and/or functional characteristics of the attached catheter 14 and compares these to predetermined criteria.

As shown in FIG. 4, the identification means 76 includes means 88 carried within the catheter handle 20 for automatically generating a uniquely coded identification signal 90 when the catheter 14 is attached to the system 10. The signal 90 is coded to uniquely identify the particular performance and/or physical characteristics of the catheter 14 and attached electrode 16.

The selected catheter characteristics identified by the code can vary. They may include electrode surface area, electrode configuration, electrode orientation, and electrode field dispersion properties. They also indicate the presence of a temperature sensor or thermistor and its associated resistance calibration value. They may simply identify catheter product numbers or other commercial designations.

The catheter identification means 88 carried within the handle can vary.

In one embodiment, the catheter identification means 88 can comprise a resistor having a prescribed ohm value, which varies according to the physical and/or performance characteristics of the catheter 14. The sensed ohm value then becomes the identification code for the catheter.

In an alternative and preferred embodiment, instead of the resistor, the catheter identification means 88 can comprise a solid state micro-chip, ROM, EEROM, EPROM, or non-volatile RAM carried within the handle 20. The micro-chip can be pre-programmed with a digital value representing the catheter identification code and other information. In this way, the catheter itself can be programmed to store information about its operational and functional characteristics.

The identification means 76 includes a register means 92 that latches the sensed catheter identification code when the catheter 14 is attached to the generator 12.

The identification means 76 also includes a catheter criteria look-up table 86 in system ROM. The table 86 specifies the catheter types that are approved for use in association with the system 10, as well as those catheter types that are not approved for use. The selection criteria takes into account the performance and/or physical characteristics necessary for safe and efficacious therapeutic use, based upon empirical testing, governmental regulatory approval, and similar relevant considerations.

The approved catheter types in the look-up table 86 are coded to correspond with the identification codes the catheter 14 carries.

Preferably, the codes in the look up table 86 further classify the physical and/or performance characteristics of different catheters 14 at different set power conditions, as determined by empirical testing.

In this arrangement, the table 86 permits the identification means 76 to distinguish between acceptable and unacceptable catheter types on an interactive basis, taking into account the particular power condition set for the generator 12.

When the identification means 76 takes into account the selected power output of the generator 12, one catheter code may be acceptable for use at low selected power outputs, whereas the same catheter code may not be acceptable at selected higher power outputs.

The identification means 76 also includes a comparator 96. The comparator 96 looks to the input 68 to determine the set power condition and compares the sensed catheter type (latched in the register means 92) with the catheter types listed in the catheter criteria table 86.

When the sensed physical and/or functional characteristics of the catheter 14 and the predetermined criteria at the set power condition match, the comparator 96 generates a first control signal 78. When the sensed physical and/or functional characteristics of the catheter 14 and the predetermined criteria at the set power condition do not match, the comparator 96 generates a second control signal 80.

The first control signal 78 enables the physician to operate the system 10 with the catheter 14 selected and at the set power condition. In addition, the first control signal 78 preferably generates a confirming, user discernible "Use Permitted" message 79.

The second control signal 80 disables or at least discourages operation of the system 10 at the set power condition. The particular operative effect of second control signal 80 can vary.

In a preferred embodiment, the second control signal 80 activates an interlock 82 that disables the power generator 12. The interlock 82 prevents operation of the system 10, thereby preventing the intended use of the catheter 14.

Alternatively, the second control signal 80 generates a user discernible "Use Not Permitted" alarm message 84 under this condition. Most preferably, the second control signal 80 simultaneously activates the interlock 82 while generating a confirming, user discernible alarm 84.

The identification means 76 also preferably serves as an information source for the physician. In this mode, the identification means 76 includes a look-up table 87 that correlates the catheter identification codes with a user readable message that contains useful physical and performance information about the selected catheter 14. The message can list the manufacturer of the catheter, the surface area and other relevant characteristics of the ablating electrode, including the presence or absence of temperature sensing elements. The message can also list the set power conditions approved or recommended for the catheter.

In this embodiment, the identification means 76 includes a second comparator 97. The comparator reads the code latched in the register means 92 looks to the table 87 to obtain the corresponding message. The comparator 97 outputs the message to a display device 99 for the physician to read.

Monitoring Catheter Use

Figure 5:
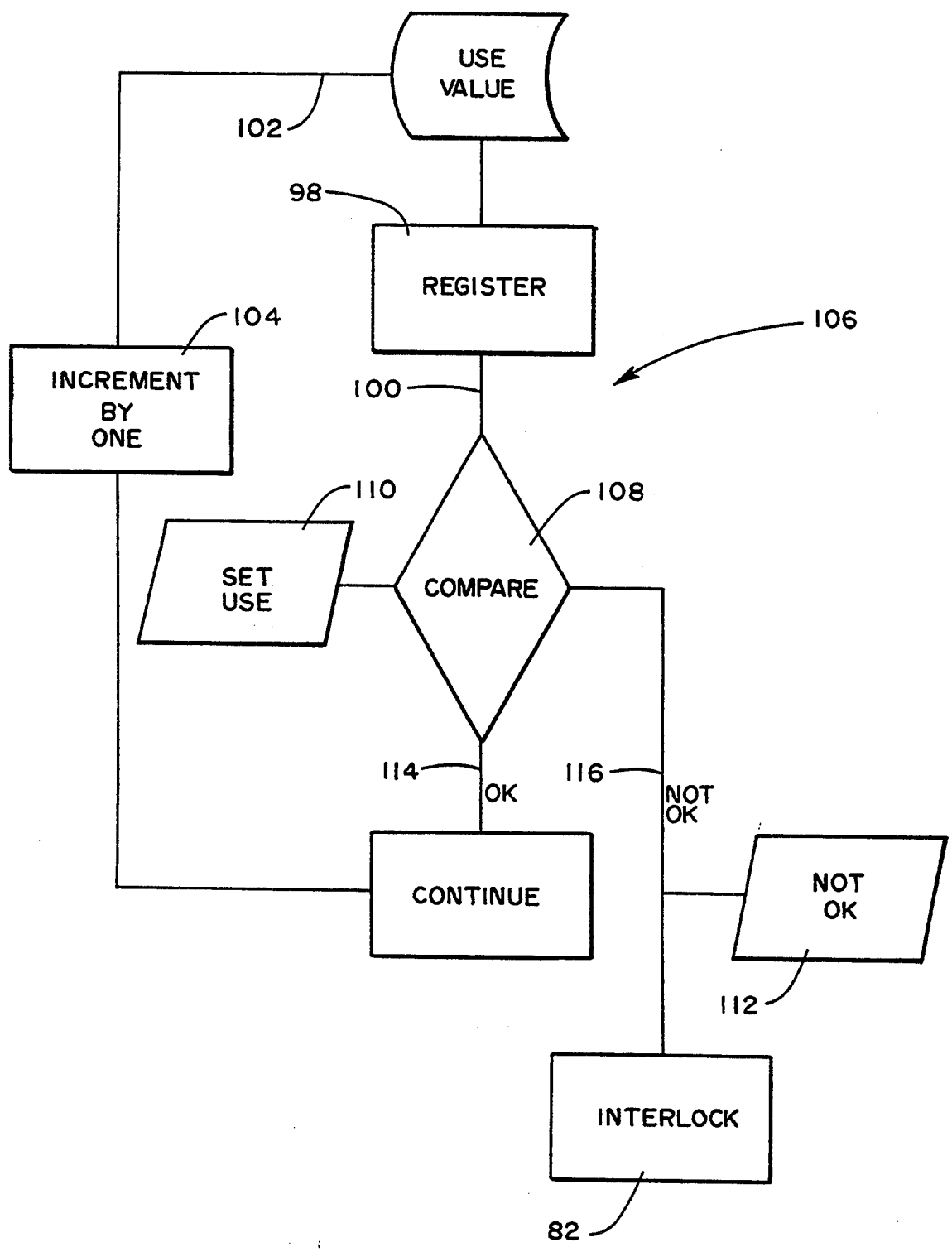
FIG. 5 is a schematic view of a catheter identification circuit that enables or prevents use of the catheter based upon prior use criteria.

As FIG. 5 shows, the identification means 76 can also serve to monitor the use of the catheter 14.

In this preferred embodiment, the identification means 76 includes a use register 98 carried within the catheter handle 20. The use register 98 latches a digital value representing the number of times the catheter 14 has been used.

Preferably, the use register 98 comprises a solid state micro-chip having non-volatile RAM carried within the catheter handle 20.

The use register 98 is initially programmed by the manufacturer with a digital value of zero. The use register 98 includes an output 100 for generating this digital value. The use register 98 also includes an input 102 for incrementing the digital value after each use.

The identification means 76 includes means 104 for incrementing by one the digital value carried by the use register 98 after each permitted use of the catheter 14.

The identification means 76 also includes means 106 for determining the digital value resident within the use register 98 before allowing use of the catheter 14 with the generator 12.

In this arrangement, the identification means 76 includes a comparator 108 that compares the resident digital value with a set value in a use criteria table 110, which represents the maximum number of uses allowed.

If the resident value is less than the set value, the comparator generates a signal 114 that permits continued use of the catheter 14 with the power generator 12.

If the resident value equals or exceeds the set value, the comparator 108 generates a signal 116 to activate the previously described power interlock 82. The interlock 82 prevents use of the catheter 14 with the generator 12.

Alternatively, the comparator 108 simply activates a display 112 to warn the physician, counseling against reuse of the chosen catheter 14. Of course, the identification means can both activate the interlock 82 and the display 112.

Various features of the invention are set forth in the following claims.

We claim:

1. A catheter including a body carrying an electrode having a predetermined operating characteristic, the body also carrying electronic means for retaining an identification code that uniquely identifies the predetermined operating characteristic of the electrode, the electronic retaining means including an output for transmitting the identification code to an external reader in response to a predetermined externally generated prompt, said electrode and said retaining means both being operatively connected to apparatus for providing power to said electrode, said apparatus further comprising said external reader, said reader being operatively connected to means for generating a control signal to permit flow of power to said electrode in response to a preselected control signal and wherein said retaining means includes a microchip holding the identification code as a digital value.

2. A catheter according to claim 1 wherein the electrode comprises a cardiac ablation electrode.

3. A catheter according to claim 1 wherein the body comprises a handle having an interior area, and
wherein the electronic retaining means is carried within the interior area of the handle.

4. A catheter according to claim 3 comprising a guide body that carries said electrode.

5. A catheter according to claim 1 wherein the electronic retaining means comprises non-volatile RAM.

6. A catheter according to claim 1 wherein the electronic retaining means comprises ROM.

7. A catheter according to claim 1 wherein the electronic retaining means comprises EPROM.

8. A system comprising
a catheter carrying an electrode having a predetermined operating characteristic, the catheter also carrying means for electronically retaining an identification code that uniquely identifies the predetermined operating characteristic of the electrode, the electronic retaining means including an output for generating the identification code in response to a predetermined externally generated prompt, and
apparatus for interaction with the electrode including means for providing power to said electrode,
said apparatus further comprising means for coupling the catheter to said apparatus for interaction therewith, and
means operative, when coupled to the catheter, for prompting the electronic retaining means to generate the identification code,
a register for registering the generated identification code,
means for storing predetermined criteria governing the interaction between the catheter and the apparatus, and
means connected to the register and the storage means for comparing the generated identification code to the predetermined interaction criteria and for generating a first control signal when the generated identification code meets the predetermined interaction criteria and for generating a second control signal, different than the first control signal, when the generated identification code does not meet the predetermined interaction criteria, the apparatus further including an interlock for permitting interaction with said catheter in response to the first control signal and for preventing interaction with said catheter in response to the second control signal.

9. A system according to claim 8
wherein the apparatus includes control means for operating in a first interaction mode with said catheter in response to the first control signal and for operating in a second interaction mode with said catheter, different than the first interaction mode, in response to the second control signal.

10. A system according to claim 8
wherein the apparatus includes means for generating a first user discernible signal in response to the first control signal and for generating a second user discernible signal, different than the first user discernible signal, in response to the second control signal.

11. A catheter including a body carrying an electrode having predetermined operating characteristic, the body also carrying electronic means for retaining a code that represents the number of times that the electrode has been used, the electronic retaining means including output means for generating said number in response to a predetermined prompt and input means for updating said number in response to each use of the electrode.

12. A catheter according to claim 11
wherein the electrode comprises a cardiac tissue ablation electrode.

13. A catheter according to claim 11
wherein the body comprises a handle having an interior area, and
wherein the electronic retaining means is carried within the interior area of the handle.

14. A catheter according to claim 13 comprising
a guide body that carries said electrode.

15. A system comprising
a catheter carrying an electrode having a predetermined operating characteristic, the catheter also carrying means for electronically retaining a usage code representing the number of times the electrode has been used, the electronic retaining means including output means for generating the usage code in response to a predetermined prompt and input means for updating the usage code, and
apparatus for interaction with the catheter including means for providing power to said electrode,
said apparatus comprising means for coupling the catheter to the apparatus for interaction therewith, including
means operative, when coupled to the catheter, for prompting the electronic retaining means to generate the usage code,
a register for registering the generated usage code,
means for storing a predetermined value representing the maximum number of times the electrode can be used, and
means connected to the register and the storage means for comparing the generated usage code to said predetermined value and for generating a first control signal when the generated usage code is less than said predetermined value and for generating a second control signal, different than the first control signal, when the generated usage code is equal to or exceeds said predetermined value, one of said control signals permitting power to flow to said electrode and one of said control signals preventing power from flowing to said electrode.

16. A system according to claim 15 wherein the apparatus includes control means for permitting operation in interaction with said catheter in response to the first control signal and for preventing the operation in interaction mode with said catheter in response to the second control signal.

17. A system according to claim 15 wherein the apparatus includes means for generating a first user discernible signal in response to the first control signal and for generating a second user discernible signal, different than the first user discernible signal, in response to the second control signal.

18. A system according to claim 15 wherein the apparatus include means for generating a signal to the input means of the electronic retaining means for updating the usage code after operation in interaction with said catheter.

19. A tissue ablation catheter including a body carrying an ablating electrode having a predetermined operating characteristic, said body also containing electronic means for retaining a code that identifies the number of times the ablating electrode has been used, the electronic retaining means including output for transmitting the usage code to an external reader in response to a predetermined prompt transmitted by said reader and input means to receive a signal transmitted by said reader for updating the usage code in response to use, said electrode, and said retaining means both being operatively connected to apparatus for providing power to said electrode, said apparatus further comprising said external reader, said reader being operatively connected to means for generating control signal to prevent flow of power to said electrode in response to a preselected control signal after a predetermined number of uses of said electrode have been recorded.

20. Apparatus for supplying energy to a tissue ablation electrode comprising
generating means for producing ablating energy for the electrode in a first power mode and in a second power mode different than the first power mode,
interchangeable catheters, a selected one of which is connected to said generating means, each of said catheters having a catheter body carrying an ablating electrode and each being provided with means for electrically connecting said electrode to the generating means,
means for registering a first control condition when an ablating electrode having a first characteristic is connected to the generating means and for registering a second control condition when an ablating electrode having a second characteristic, different than the first characteristic, is connected to the generator means, and
control means operatively connected to and responsive to the register means for operating the generating means in the first power mode when the first control condition is registered and for operating the generating means in the second power mode when the second control condition is registered.

21. Apparatus according to claim 20 wherein said generating means comprises a radio frequency generator.

* * * * *